(12) United States Patent
Norvell

(10) Patent No.: US 11,484,482 B1
(45) Date of Patent: Nov. 1, 2022

(54) TATTOO INK FORMULATION

(71) Applicant: Michelle Norvell, Las Vegas, NV (US)

(72) Inventor: Michelle Norvell, Las Vegas, NV (US)

( * ) Notice: Subject to any disclaimer, the term of this patent is extended or adjusted under 35 U.S.C. 154(b) by 0 days.

(21) Appl. No.: 17/233,459

(22) Filed: Apr. 17, 2021

Related U.S. Application Data

(60) Provisional application No. 63/012,366, filed on Apr. 20, 2020.

(51) Int. Cl.
*A61Q 1/00* (2006.01)
*A61K 8/20* (2006.01)
*A61Q 1/02* (2006.01)
*A61K 8/49* (2006.01)
*A61K 8/46* (2006.01)
*A61K 8/42* (2006.01)
*A61M 37/00* (2006.01)
*A61K 8/44* (2006.01)
*A61K 8/41* (2006.01)

(52) U.S. Cl.
CPC ............ *A61K 8/20* (2013.01); *A61K 8/41* (2013.01); *A61K 8/42* (2013.01); *A61K 8/44* (2013.01); *A61K 8/447* (2013.01); *A61K 8/46* (2013.01); *A61K 8/466* (2013.01); *A61K 8/496* (2013.01); *A61K 8/4913* (2013.01); *A61K 8/4926* (2013.01); *A61M 37/0076* (2013.01); *A61Q 1/025* (2013.01)

(58) Field of Classification Search
CPC ................................ A61Q 1/025; A61Q 1/145
USPC ........................................................ 106/31.03
See application file for complete search history.

(56) References Cited

U.S. PATENT DOCUMENTS

| | | | |
|---|---|---|---|
| 2009/0071365 A1* | 3/2009 | Agrawal | A61K 8/498 106/31.03 |
| 2016/0128919 A1* | 5/2016 | Sveine | A45D 34/042 401/268 |
| 2017/0014317 A1* | 1/2017 | Youngbull | A61K 8/8141 |

* cited by examiner

*Primary Examiner* — Eisa B Elhilo
(74) *Attorney, Agent, or Firm* — Gulf Coast Intellectual Property Group

(57) ABSTRACT

The present invention provides three embodiments to create and apply a tattoo to a dermal area of a recipient wherein the tattoo is non-permanent. The present invention includes a first embodiment and a second embodiment wherein the tattoo ink is removable via introduction of a solution and/or a solvent. A third embodiment of the present invention provides a method for tattoo ink creation that provides a tattoo ink that will degrade within the aqueous bodily environment over a period of time based on the polymer with which the water soluble dye is created. The first embodiment utilizes an organic dye that contains at least one metal atom. A solution containing a chelating agent is presented to the tattooed area wherein the chelating agent will extract the metal atom resulting in disappearance of the tattoo ink. Another embodiment utilizes wax encapsulated ink to be removed by presentation of a solvent.

15 Claims, 3 Drawing Sheets

TATTOO INK FORMULATION

PRIORITY UNDER 35 U.S.C SECTION 119 (E) & 37 C.F.R. SECTION 1.78

This nonprovisional application claims priority based upon the following prior United States Provisional Patent Application entitled: Tattoo Ink Formulation, Application No.: 63/012,366 filed Apr. 20, 2020, in the name of Michelle Norvell, which is hereby incorporated by reference for all purposes.

FIELD OF THE INVENTION

The present invention relates generally to tattooing, more specifically but not by way of limitation, a tattoo ink formulation wherein the tattoo ink of the present invention includes alternate embodiments wherein two embodiments have a formulation that are structured for subsequent treatment to decolorize a tattoo and an additional embodiment that decolorizes over time ensuing application.

BACKGROUND

As is known in the art, tattooing goes back as far as back as Neolithic times. Ancient tattooing was performed for various cultural and religious reasons and utilized primitive tools such as fish bones to pierce the skin and apply ink thereto. The word tattoo is derived from the Tahitian word, tatau, and was introduced into the English language subsequent one of Captain James Cook's expeditions to the South Pacific. Over the past three decades tattooing has become more popular in the United States and the practice has crossed social boundaries and having a tattoo is considered more socially acceptable than in the past. Artists create tattoos by injecting ink into a person's skin. To accomplish this the artist will utilize a needle that punctures skin at a rate of 50 to 3000 times per minute. The needle typically is calibrated to penetrate the skin about a millimeter and deposits a drop of insoluble ink.

One issue with tattooing is the permanence of the ink. Once an individual chooses to have a tattoo it is permanent and if desired to be removed can be a painful and costly procedure. Tattoo inks are manufactured from materials such as but not limited to titanium dioxide. These materials are designed to be permanent. If a person decides they no longer wish to have the tattoo, the removal procedure can be expensive and painful. The standard modality for tattoo removal involves the utilization of Q-switched lasers. The laser have been proven to be generally successful at removing most pigments but the patient still endures a significant amount of discomfort during the removal process.

It is intended within the scope of the present invention to provide a tattoo ink formulation and embodiments thereof wherein the tattoo ink of the present invention is formulated to fade over time or be removed wherein the removal involves the use of injectable solutions that cause the color of the tattoo to disappear.

SUMMARY OF THE INVENTION

It is the object of the present invention to provide a tattoo ink formulation that is structured to provide improved removal thereof wherein the formulation of the present invention includes an organic dye containing a metal atom.

Another object of the present invention is to provide a tattoo ink having a formulation permitting extraction of the metal atom contained therein wherein the tattoo ink is formulated to have the metal atom contained therein extracted via exposure to chelating agents.

A further object of the present invention is to provide a tattoo ink formulation that is structured to provide improved removal thereof wherein the formulation of the present invention facilitates breakdown of the chromaphore and as such decolorize the tattoo present in a person's epidermal layer.

Still another object of the present invention is to provide a tattoo ink having a formulation permitting extraction of the metal atom contained therein wherein the chelating agents operable to decolorize the tattoo retain water solubility subsequent coordinating to a transition metal.

An additional object of the present invention is to provide a tattoo ink formulation that is structured to provide improved removal thereof wherein the tattoo ink of the present invention can be decolorized ensuing subcutaneous injections of sterile aqueous solutions at the tattoo site.

Yet a further object of the present invention is to provide a tattoo ink having a formulation permitting extraction of the metal atom contained therein wherein an embodiment of the aqueous solution can include 0.9% sodium chloride and a metal chelating agent.

Another object of the present invention is to provide a tattoo ink formulation that is structured to provide improved removal thereof wherein an alternative embodiment of the aqueous solution can comprise a 0.9% sodium chloride, a chelating agent and an epidermal penetrating solvent such as but not limited to N-methylpyrrolidone.

An alternate object of the present invention is to provide a tattoo ink having a formulation based upon water soluble pigments encapsulated by a hard wax wherein the tattoo pigment is suitable for suspension in a viscous aqueous medium.

Still a further object of the present invention is to provide a water soluble pigment based tattoo ink formulated to facilitate subsequent decolorization thereof wherein the formulation of the present invention includes water soluble pigments formed in a suspension with a wax such as but not limited to a microcrystalline wax.

A further object of the present invention is to provide a tattoo ink having a formulation based upon water soluble pigments encapsulated by a hard wax wherein the pigment composition of the present invention is processed with a drying tool operable to provide atomization thereof and form minute spherical droplets that will harden subsequent cooling.

An alternative objective of the present invention is to provide a water soluble pigment based tattoo ink formulated to facilitate subsequent decolorization thereof wherein the wax coating of the pigment spherical droplets is a hydrophobic wax that is dissolvable via solvents.

Another object of the present invention is to provide a tattoo ink having a formulation based upon water soluble pigments encapsulated by a hard wax wherein a solvent infusion into the epidermal layer where present will results in compromise of the wax coating and as such facilitate the decolorization of the tattoo.

Yet a further object of the present invention is to provide a tattoo pigment formulation that is configured to decolorize over a specified time period wherein the pigment of the present invention is suitable for suspension in a viscous aqueous medium.

Another object of the present invention is to provide a tattoo pigment formulation based on a water soluble core having a biodegradable polymer jacket wherein the embodiment includes combining a water soluble dye with a polymer such as but not limited to polyvinyl alcohol.

An additional object of the present invention is to provide a tattoo pigment formulation that is configured to decolorize over a specified time period wherein the water soluble dye is combined with a polymer wherein the polymer has been heated in excess of its melting point.

An alternative objective of the present invention is to provide a tattoo pigment formulation based on a water soluble core having a biodegradable polymer jacket wherein the preferred polymer has an average molecular weight between 15,000 and 20,000.

Still a further object of the present invention is to provide a tattoo pigment formulation that is configured to decolorize over a specified time period wherein the process of the present invention further includes combining a ground colored polyvinyl alcohol with a biodegradable polymer.

Yet another object of the present invention is to provide a tattoo pigment formulation based on a water soluble core having a biodegradable polymer jacket wherein the preferred biodegradable polymer has a melting point of 59 to 64 degrees Celsius.

An additional object of the present invention is to provide a tattoo pigment formulation that is configured to decolorize over a specified time period wherein the formulation retains separation between two polymers facilitating a pigment creation that exhibits a distinct end point time of dissolution.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
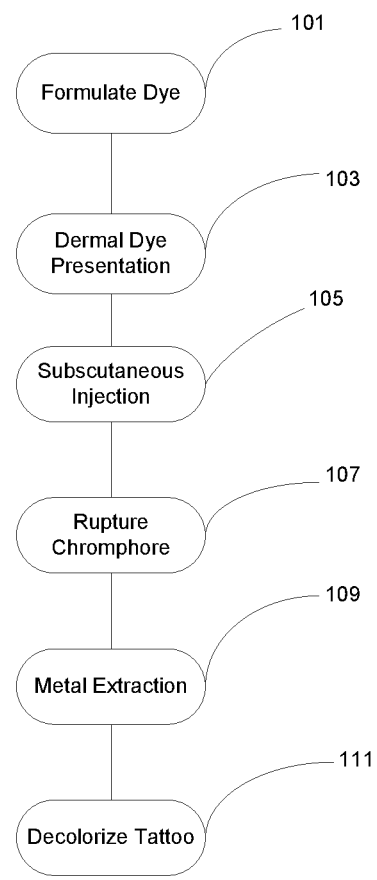
FIG. 1 is a diagram of the first embodiment of the present invention.

Referring now to the drawings submitted herewith, wherein various elements depicted therein are not necessarily drawn to scale and wherein through the views and figures like elements are referenced with identical reference numerals, there is illustrated a tattoo ink formulation 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring now to the drawings submitted as a part hereof, the tattoo ink formulation 100 includes three embodiments to accomplish the desired objective of the present invention to provide a tattoo ink that is semi-permanent and/or removable based on presentation of an antidote. Following is a discussion on the three embodiments of the present invention. The first embodiment of the present invention includes tattoo ink formulation that utilizes an organic dye wherein the organic dye of the tattoo ink formulation includes a metal atom. The metal atom of the tattoo ink formulation of the present invention can be copper, cobalt or chromium. Step 101 of the ink formulation will be to formulate an organic dye wherein the organic dye will contain a single atom of copper, cobalt or chromium per molecule of dye. It should be understood within the scope of the present invention that the ink formulation could occur in various alternate volumes. In step 103, the ink formulation is presented dermally to a recipient wherein the recipient will receive an amount of the ink formulation within the dermis so as to have a tattoo presented on their skin. It should be understood within the scope of the present invention that a full palate of colors is provided for the ink formulation of the present invention wherein the ink formulation includes a spectral order from longest wave length expressed to the shortest wave length expressed in order to achieve the desired colors of the ink formulation.

In step 105, once a recipient of the ink formulation has decided to no longer have the tattoo created by presentation of the ink formulation of the present invention a solution configured to treat heavy metal intoxication will be provided via subcutaneous injection to the recipient in the area of the tattoo. The solution includes strong chelating agents that retain good water solubility after coordinating to a metal. In step 107, exposure of the metal containing tattoo pigments to these chelating agents will cause the copper, chromium or cobalt atom present in the ink formulation of the present invention to rupture the chromaphore. The tattoo dyes may be exposed to one or more of the strong chelating agents by subcutaneous injection of a sterile aqueous solution consisting of 0.9% sodium chloride and a metal chelating agent. In an alternative method for execution of Step 105, the tattoo may be removed by treating the tattooed area with a sterile aqueous solution consisting of 0.9% sodium chloride, a strong chelating agent and an epidermal penetrating solvent such as N-methylpyrrolidone, DMSO or N, N-dimethylacetamide. The epidermal penetrating solvent will drive the strong chelating agent into the dermis where the dyes forming the tattoo are present and as such result in extraction of the metal atom resulting in the fading of the color of the tattoo. In step 109, ensuing exposure to the chelating agent, the metal atom will be extracted and as such lead to the fading of the color of the tattoo created by the ink formulation of the present invention. Step 111, the tattoo is permanently de-colorized via exposure to the solution of the present invention containing the chelating agent. While various chelating agents can be utilized to achieve the aforementioned, good results have been achieved utilizing the following chelating agents: N-Acetylcysteine, Deferoxamine, Deferiprone, Deferasirox, Dimercaptopropane-1-sulfonic Acid, Diethylenetriaminepentaacetate, Ethylenediaminetetraacetic Acid Disodium Salt, D-Penicillamine, Trientine, 2,3-Dimercaptosuccinic acid and 2,3-Dimercaprol.

Figure 2:
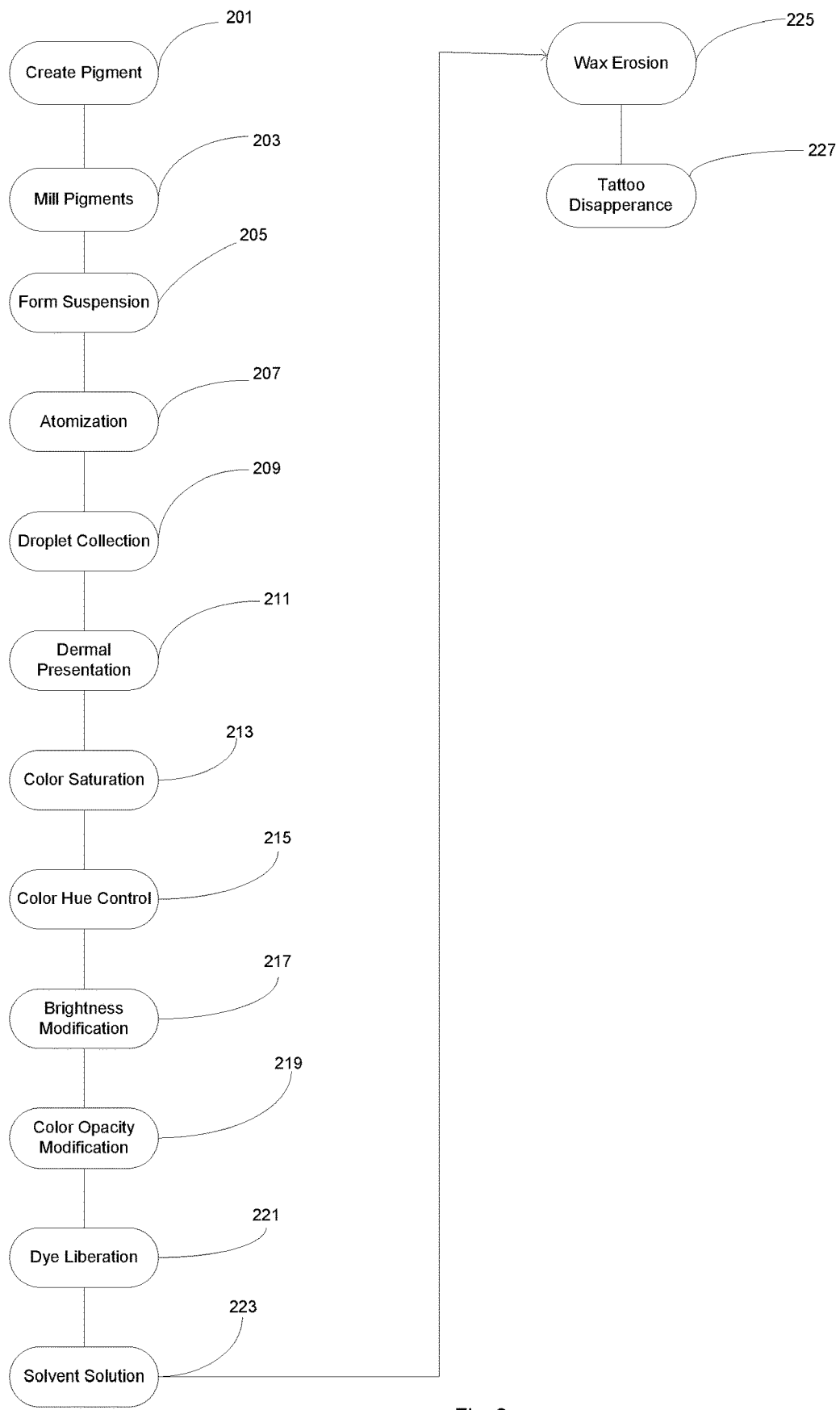
FIG. 2 is a diagram of the second embodiment of the present invention.

Referring now to FIG. 2, an outline of the second embodiment of the present invention is diagrammed therein. Step 201, A tattoo pigment suitable for suspension in a viscous aqueous medium is created by combining water soluble pigments accepted for use in compounding pharmaceutical materials and in food preparation with a suitable hard wax. Step 203, the water-soluble pigments should first be milled to a very fine powder of 800 mesh or smaller prior to combining such pigments with melted bees wax, microcrystalline wax or carnauba wax. In step 205, the pigments will form a suspension within the wax wherein the wax protects the pigment from dissolving in the aqueous bodily environment of a human. Step 207, ensuing creation of the pigment composition, the hot liquid material is forced through an appropriate spray drying tool using compressed air. This will atomize the composition, leading to the formation of minute spherical droplets that will harden as they cool while traveling from the spray nozzle to a collection container. This spray drying process is regulated through selection of air pressure and spray dry tool orifice size so that droplets falling within the size range of 50 to 500 microns are produced in step 209. In step 211, the droplets are sufficiently small so that they will create uniform coloration when emplaced within the dermis with a tattooing needle. Step 213, the color saturation of the pigment may be controlled by varying the weight ratio of solid water soluble dye to wax. In step 215, the color hue is controlled by selecting one or more dyes to form a particular pigment composition. Step 217, color brightness is modified through the incorporation of an optical brightener. In step 219, color opacity is modulated via the addition of small quantities of a black dye to an ink formulation.

Tattoo pigments consisting of water soluble dyes encased within a hydrophobic wax coating, as described herein above, are vulnerable to solvents that cause the wax to soften and liquefy. In step 221, liberation from the encapsulating wax will cause the removal of the water soluble dyes from the body directly by the kidney or through conjugation of the dye in the liver with one or more molecules of glucose followed by removal via the kidney. Solvents used in this application must be benign as they will be infused into tissue. Solvents capable of attacking the integrity of wax particles while not exhibiting a high level of cytotoxicity include but are not limited to: glycol ethers, triethylene glycol dimethyl ether, tetraethylene glycol dimethyl ether, cyrene and dimethyl isosorbide. Step 223, the aforementioned solvent materials are be combined with skin penetrating solvents to create a solvent solution that are applied directly to the skin. Epidermal penetrating solvents such as N-methylpyrrolidone, dimethyl sulfoxide (DMSO) and N, Ndimethylacetamide will facilitate the infiltration of one or more solvents selected from the aforementioned list into the dermis of the tattoo recipient. In step 225, the solvent erodes the integrity of the wax and softens the tattoo pigment. Step 227, as the wax pigment particles lose integrity, the water soluble dyes will leak out and dissolve into the interstitial fluid and as such result in the disappearance of the tattoo.

Figure 3:
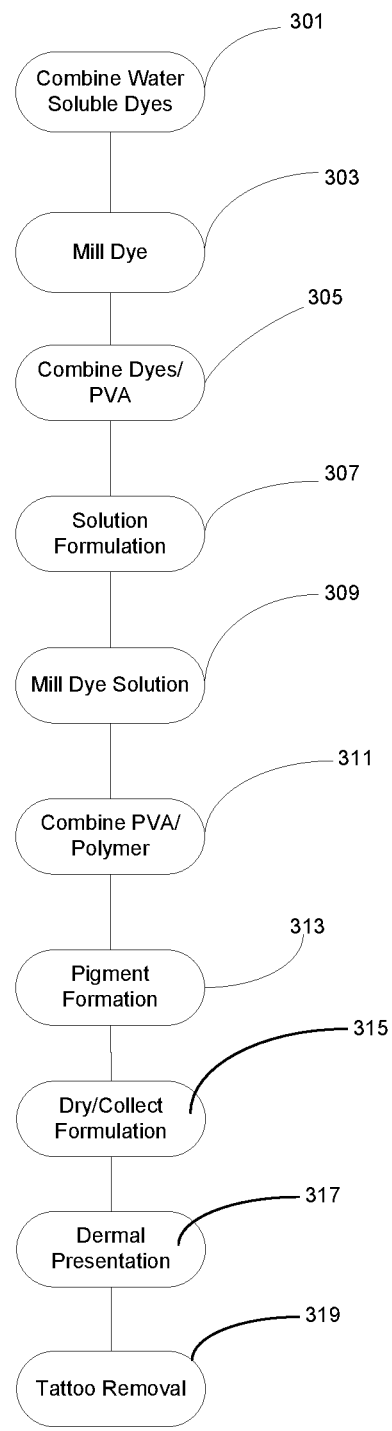
FIG. 3 is a diagram of the third embodiment of the present invention.

Now referring to FIG. 3 herein, the third embodiment of the present invention is outlined therein. The third embodiment of the present invention is a self-erasing tattoo pigment having a water soluble core encased in a biodegradable polymer jacket. In the third embodiment of the present invention, the tattoo pigment suitable for suspension in a viscous aqueous medium is created through a two-step process. In step 301, the first step consists of combining water soluble dyes already accepted for use in compounding pharmaceutical materials and in food preparation with a polymer referred to as polyvinyl alcohol. Step 303, the water soluble dyes are be milled to a very fine powder of 800 mesh or smaller prior. In step 305, the water soluble dyes are combined with a medium molecular weight polyvinyl alcohol that has been heated to a temperature a few degrees in excess of its melting point. Polyvinyl alcohol melts within a range of 190 to 200 degrees Celsius depending upon the specific grade and molecular weight selected. In step 307, the dyes will form a solid solution with the medium molecular weight polyvinyl alcohol. Step 309, ensuing cooling, the colored solid polyol dye solution should be milled to a very fine powder with an average particle size of 20 microns or less before using it in the next step. The specific polyvinyl alcohol recommended for this application has an average molecular weight of between 15,000 and 20,000. This type of polyvinyl alcohol retains excellent water solubility and is readily purged from the body via the kidneys. In step 311, the ground colored polyvinyl alcohol should be combined with a biodegradable polymer wherein the polymer has been heated to a temperature a few degrees in excess of its melting point. Step 313, this results in the formation of the pigment composition. In step 315, the hot material should be forced through an appropriate spray-drying tool using compressed air. This will atomize the composition, leading to the formation of minute spherical droplets that will harden as they cool while traveling from the spray nozzle to a collection container. The spray drying process is regulated through selection of air pressure and spray dry tool orifice size so that droplets falling within the size range of 50 to 500 microns are produced. These droplets are sufficient in size so as to create uniform coloration when emplaced within the dermis with a tattooing needle in step 317.

The color saturation of the pigment may be controlled by varying the weight ratio of solid water soluble dye to polyvinyl alcohol. The color hue may be controlled by selecting one or more dyes to form a particular pigment composition. Color brightness can be modified through the incorporation of an optical brightener. Finally, color opacity can be modulated via the addition of small quantities of black dye to the pigment formulation. The full palate of water soluble colors available was presented in the previous section of this document. The final product is a tattoo pigment, which will self-erases within a predictable time. That time is controlled by selection of the biodegradable polymer. A wide variety of biodegradable polymers are available and it should be understood within the scope of the present invention that the various alternate types could be utilized. Each biodegradable polymer has a predictable time over which the polymer will degrade within a living environment, ranging from a few months to several years. Once the protective biodegradable polymer has been degraded, it will no longer afford protection to the medium molecular weight polyvinyl alcohol core that contains dye from the aqueous bodily environment. In step 319, the polyvinyl alcohol and dyes will dissolve in the interstitial fluid and be removed without any further intervention. While no particular biodegradable polymers is required, the biodegradable polymer recommended to coat the dye carrying polyvinyl alcohol particles is poly-caprolactone. Poly-caprolactone has a melting range from 59 to 64 degrees Celsius. The low melting point range of poly-caprolactone will allow the granules of dye dispersed within polyvinyl alcohol to remain in distinct form when the poly-caprolactone is applied in molten form. Retaining separation between the two polymers provides for the creation of a pigment that exhibits a distinct end point in time for its dissolution and as such tattoo removal.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding description is, therefore, not intended to be limited to the specific forms set forth herein, but on the contrary, it is intended to cover such alternatives, modifications, and equivalents, as can be reasonably included within the spirit and scope of the invention.

What is claimed is:

1. A method of formulating a tattoo ink wherein the tattoo ink is operable to be removed ensuing exposure to a chelating agent wherein the method comprises the steps of:
   selecting an organic dye, wherein the organic dye includes at least one metal atom as part of the composition structure thereof;
   injecting the organic dye into a dermal area of a recipient, wherein the organic dye is introduced into the dermal area through utilization of a tattoo needle;
   selecting a chelating agent solution;
   injecting the chelating agent solution, wherein the chelating agent solution is injected into the dermal area having the organic dye present therein;
   rupturing a chromaphore, wherein the chelating agent solution will result in rupture of the chromaphore;
   extracting the metal, wherein the chelating agent solution will extract the at least one metal atom from the organic dye;
   removing the organic dye, wherein the organic dye creating a tattoo in the dermal area is dissolved so as to result in removal of the tattoo from the dermal area.

2. The method of formulating a tattoo ink wherein the tattoo ink is operable to be removed ensuing exposure to a chelating agent as recited in claim 1, and further including the step of presenting an aqueous solution to the dermal area, wherein the aqueous solution consists of a 0.9% sodium chloride, a chelating agent and an epidermal penetrating solvent.

3. The method of formulating a tattoo ink wherein the tattoo ink is operable to be removed ensuing exposure to a chelating agent as recited in claim 2, wherein the epidermal penetrating solvent is selected from a group consisting of one of the following: Nmethylpyrrolidone, DMSO or N,N-dimethylacetamide.

4. The method of formulating a tattoo ink wherein the tattoo ink is operable to be removed ensuing exposure to a chelating agent as recited in claim 3, wherein the chelating agent solution contains a chelating agent selected from a group consisting of one of the following: N-Acetylcysteine, Deferoxamine, Deferiprone, Deferasirox, Dimercaptopropane-1-sulfonic Acid, Diethylenetriaminepentaacetate, Ethylenediaminetetraacetic Acid Di sodium Salt, D-Penicillamine, Trientine, 2,3-Dimercaptosuccinic acid or 2,3-Dimercaprol.

5. The method of formulating a tattoo ink wherein the tattoo ink is operable to be removed ensuing exposure to a chelating agent as recited in claim 4, wherein the tattoo ink is provided in a plurality of colors.

6. A method of applying a tattoo to a dermal area of a recipient wherein the tattoo is comprised of ink vulnerable to solvent so as to facilitate removal of the tattoo wherein the method comprises the steps of:
   creating a pigment, wherein the pigment is a water soluble dye;
   milling the pigment, wherein the pigment is milled to a powder;
   combining the pigment with a wax, wherein subsequent the milling of the pigment the pigment is combined with a wax so as to encapsulate the water soluble dye;
   forming a suspension, wherein ensuing the combination of the wax and pigment a suspension is formed so as to create a composition;
   atomizing the composition, wherein the composition is forced through a compressed air spray dryer to form spherical droplets;
   collecting the droplets;
   presenting the droplets into the dermal area so as to create the tattoo;
   applying a solvent, wherein the solvent is presented to the dermal area having the tattoo;
   liberating the water soluble dye, wherein the solvent dissolves the wax encapsulation surrounding the water soluble dye; and
   removing the tattoo, wherein the water soluble dye is removed from the dermal area directly by a kidney of the recipient or through conjugation of the dye in the liver.

7. The method of applying a tattoo to a dermal area of a recipient wherein the tattoo is comprised of ink vulnerable to solvent as recited in claim 6, wherein the droplets are formed within the size range of 50 to 500 microns.

8. The method of applying a tattoo to a dermal area of a recipient wherein the tattoo is comprised of ink vulnerable to solvent as recited in claim 7, and further including the step of controlling color saturation of the pigment, wherein the color saturation is controlled by varying a weight ratio of water soluble dye to wax.

9. The method of applying a tattoo to a dermal area of a recipient wherein the tattoo is comprised of ink vulnerable to solvent as recited in claim 8, and further including the step of controlling a color, wherein the color hue is controlled by selecting one or more dyes to form a pigment composition.

10. The method of applying a tattoo to a dermal area of a recipient wherein the tattoo is comprised of ink vulnerable to solvent as recited in claim 9, and further including the step of adding an optical brightener, wherein the optical brightener impacts brightness of the ink.

11. The method of applying a tattoo to a dermal area of a recipient wherein the tattoo is comprised of ink vulnerable to solvent as recited in claim 10, and further including the step of modulating color opacity, wherein the color opacity is modified through addition of black ink to the water soluble dye.

12. A method of creating and applying a self-erasing tattoo ink for creation of tattoos in a dermal area of a recipient wherein the method comprises the steps of:
    milling a water soluble dye, wherein the water soluble dye is milled to 800 mesh or less;
    combining the water soluble dye with a polymer;
    forming a solution, wherein the water soluble dye will form a solution with the polymer;
    cooling the solution; wherein cooling of the solution allows for milling to a powder with an average particle size of 20 microns or less for the solution;
    atomizing the solution; wherein the solution is atomized through a compressed air sprayer so as to form droplets;
    collecting the droplets, wherein the droplets are collected for use by a tattoo needle;
    applying the droplets to the dermal area, wherein the droplets are applied utilizing the tattoo needle to the dermal area;
    degrading the polymer, wherein polymer is biodegradable, ensuing degradation of the biodegradable polymer has been degraded, the polymer no longer provides protection of the water soluble dye to a aqueous bodily environment.

13. The method of creating and applying a self-erasing tattoo ink for creation of tattoos in a dermal area as recited in claim 12, wherein the droplets are within a size range of 50 to 500 microns.

14. The method of creating and applying a self-erasing tattoo ink for creation of tattoos in a dermal area as recited in claim 13, wherein the polymer is polyvinyl alcohol.

15. The method of creating and applying a self-erasing tattoo ink for creation of tattoos in a dermal area as recited in claim 14, wherein the polyvinyl alcohol has an average molecular weight of between 15,000 and 20,000.

* * * * *